United States Patent
Jacobs et al.

(10) Patent No.: US 6,735,279 B1
(45) Date of Patent: May 11, 2004

(54) SNAPSHOT BACKSCATTER RADIOGRAPHY SYSTEM AND PROTOCOL

(75) Inventors: Alan M. Jacobs, Gainesville, FL (US); Edward T. Dugan, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 10/348,487

(22) Filed: Jan. 21, 2003

(51) Int. Cl.[7] .............................................. G01N 23/201
(52) U.S. Cl. ............................................ 378/86; 378/87
(58) Field of Search ............................ 378/57, 70, 76, 378/86, 87, 88, 89, 90; 250/358.1, 370.08, 370.09, 390.01, 390.06, 253

(56) References Cited

U.S. PATENT DOCUMENTS

| | | | | |
|---|---|---|---|---|
| 4,864,142 A | * | 9/1989 | Gomberg | 250/390.04 |
| 4,918,315 A | * | 4/1990 | Gomberg et al. | 250/390.04 |
| 5,940,468 A | * | 8/1999 | Huang et al. | 378/57 |
| 6,424,695 B1 | * | 7/2002 | Grodzins et al. | 378/87 |

OTHER PUBLICATIONS

Jacobs, A.M. et al., Detection/identification of land mines by lateral migration radiography; Detection and Abandoned Land Mines, 1998. Second International Conference of the (IEE Conf. Publ. No. 458), Oct. 12–14, 1998, pages(s): 152–156.*

Lockwood, G.J. et al., Field tests of X–ray backscatter mine detection Detection of Abandoned Land Mines, 1998. Second International Conference on the (IEE Conf. Publ. No. 458), Oct. 12–14, 1998, pages(s): 160–163.*

MacDonald, Jacqueline et al., Alternatives for Landmine Detection, MR–1608–OSTP, (2003)—Jacobs, A. et al., X–ray Backscatter (Paper II)—Appendix M. page(s) 205–223.*

Towe et al., "X–Ray Backscatter Imaging," IEEE Trans., on Biomed.–Engr., BME–28, 9:646–650, 1981.

Kenney et al., Research Techniques in Nondestructive Testing, Chapter 6, "Dynamic Radiography for Nondestructive Testing," Edited by Sharpe, Academic Press, 217–243, 1977.

* cited by examiner

*Primary Examiner*—Edward J. Glick
*Assistant Examiner*—Courtney Thomas
(74) *Attorney, Agent, or Firm*—Akerman Senterfitt

(57) ABSTRACT

A snapshot backscatter radiography (SBR) system and related method includes at least one penetrating radiation source, and at least one radiation detector. The radiation detector is interposed between an object to be interrogated and the radiation source. The radiation detector transmits a portion of the forward radiation from the radiation source to the object. A portion of the transmitted radiation is scattered by the object and is detected by the detector. An image of the object can be obtained by subtracting the forward radiation detected at the detector, or an estimate thereof, from a total of all radiation detected by the detector. Integrated circuit inspection, land mine detection, and luggage or cargo screening systems can be SBR based.

24 Claims, 4 Drawing Sheets

PRIOR ART

PRIOR ART

SNAPSHOT BACKSCATTER RADIOGRAPHY SYSTEM AND PROTOCOL

CROSS-REFERENCE TO RELATED APPLICATIONS

Not applicable.

STATEMENT REGARDING FEDERALLY SPONSORED RESEARCH OR DEVELOPMENT

Not applicable.

1. Field of the Invention

The invention relates to radiography, and more particularly to radiography systems which combine aspects of both transmission and backscatter radiography, and methods thereof.

2. Background

In many industrial, military, security or medical applications, images of the internal structure of objects is required. Radiography is often used for imaging. Radiography generally comprises either conventional transmission radiography or backscatter radiography.

FIG. 1 is a schematic illustrating the configuration used for conventional transmission radiography. In conventional radiography, an image is formed by transmitting radiation from a radiation generator 105 through an internal detail 110 within object 130. Attenuated radiation is received by a radiation detector 115 which is disposed on the side of the object opposite to that of the radiation generator 105. In the case of tomography, the object 130 is generally rotated about axis perpendicular to the plane of the figure.

FIG. 2 is a schematic illustrating the configuration used for backscatter radiography. Unlike conventional radiography which relies on transmission, in backscatter radiography radiation is scattered by internal detail 210 within object 230. In backscatter radiography, the radiation generator 205 and radiation detector 215 are on the same side of the object 230. All backscatter radiography techniques allow one-sided imaging of the object since the radiation generator 205 and the radiation detector 215 are located on the same side of the object 230. This is the same imaging configuration that people and animals use for optical viewing of the surroundings. Because of the absence of a refraction process for the penetrating radiation in backscatter radiography, image-gathering lenses cannot be used.

In backscatter radiography, illumination of an entire region of the object to be interrogated in a single snapshot has generally only been possible using a pinhole, coded aperture, or a restriction positioned between the object and the radiation detector. This generally results in either extremely inefficient sensing of the radiation, or the introduction of substantial image-obscuring structured noise, thus requiring large exposure times for typical radiation sources. An alternative includes use of a scanning pencil or fan beam for illuminating a temporal sequence of points or lines on the object surface. This also yields long exposure times and decoding algorithms having long calculation times, besides requiring an expensive scanning apparatus.

The equivalent of an optical snapshot camera capable of implementation using relatively inexpensive components which would provide high image resolution and a short exposure time would be desirable for applications which require one-sided imaging of the internal structure of objects.

SUMMARY OF THE INVENTION

A snapshot backscatter radiography (SBR) system and related method includes at least one penetrating radiation source and at least one radiation detector. The radiation detector is interposed between the object to be interrogated and the radiation source. The radiation detector transmits a portion of radiation received from the radiation source to the object. The object backscatters at least a portion of the radiation it receives, with a portion of the scattered radiation being detected by the detector.

Generally, reference (base) radiation data is obtained by using the system without the object present in a low backscatter environment. The base data is then preferably stored prior to interrogating the object. The base data can then be subtracted from the total radiation data measured by the detector which includes information from both the detector structure and spatial variation of the radiation source field, as well as the object structure. This permits generation of an image of the object. The system can interrogate a wide variety of objects or volumes, such as buried or otherwise unobservable volumes suspected of containing a bomb (e.g. landmine), luggage or cargo, or integrated circuits.

The penetrating radiation source can comprise an x-ray, gamma ray, neutron or an electron beam source. The detector can comprise a photostimuable phosphorous-based image plate or an amorphous silicon panel. The detector can also include a digitizing field screen. The system preferably includes a computer for receiving radiation data from the detector and for performing data and image processing A radiation source controller is also preferably provided. The radiation source controller can permit the system to produce 3 dimensional (3-D) radiation data which permits the generation of a 3-D image of the object. For example, the radiation source controller can direct the radiation source to provide multiple bursts at varying radiation energy or temporal variation of a radiation energy spectrum.

The system can also include one or more collimating sheets disposed between the object and the detector. Collimating sheet(s) can be used to improve resolution or help isolate a lateral migration component of the backscattered radiation.

A snapshot backscatter radiography (SBR) based land mine detection system includes at least one penetrating radiation source and at least one radiation detector, wherein the radiation detector is interposed between a volume of earth to be interrogated and the radiation source. The radiation detector transmits a portion of incident radiation from the radiation source to an object buried in the volume of earth, wherein a portion of radiation scattered by the object is detected by the detector. The radiation source preferably comprises an x-ray source. The radiography system can include a vehicle to add mobility to the system.

The invention can also be used for luggage or cargo screening, or as an integrated circuit inspection tool. In the case of the integrated circuit inspection tool the detector can comprise a CCD array detector. In a preferred embodiment the penetrating radiation source provides selectable radiation energy. This permits generation of a 3-D image of the object interrogated to obtained without physically scanning the system or the object by compiling radiation data at a plurality of radiation energies.

A snapshot backscatter radiography (SBR) method for imaging an object includes the steps of directing penetrating forward radiation through a detector to an object to be interrogated, the detector transmitting a portion of the penetrating radiation to the object, wherein the object backscatters radiation toward the detector. By processing the radiation data collected by the detector an image of the object can be generated. When at least one collimating sheet is disposed between the object and the detector, the method can include the step of collimating the forward radiation and/or the backscattered radiation. A deconvolving image enhancement technique can in addition be applied to reduce image blurring.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

A snapshot backscatter radiography (SBR) system and related method includes at least one penetrating radiation source, and at least one radiation detector. The radiation detector is interposed between the object to be interrogated and the radiation source so that the radiation detector receives and detects the radiation from the radiation source before transmitting a portion thereof to the object to be interrogated. The object backscatters a portion of the transmitted radiation. A portion of the backscattered radiation is detected by the detector. An image of the object can be obtained by subtracting the incident radiation data, or an estimate thereof, from the total detector data collected. Alternatively, an image of the object can be obtained by subtracting suitably normalized radiation data, or an estimate thereof, from the backscatter data collected by the detector.

Figure 1:
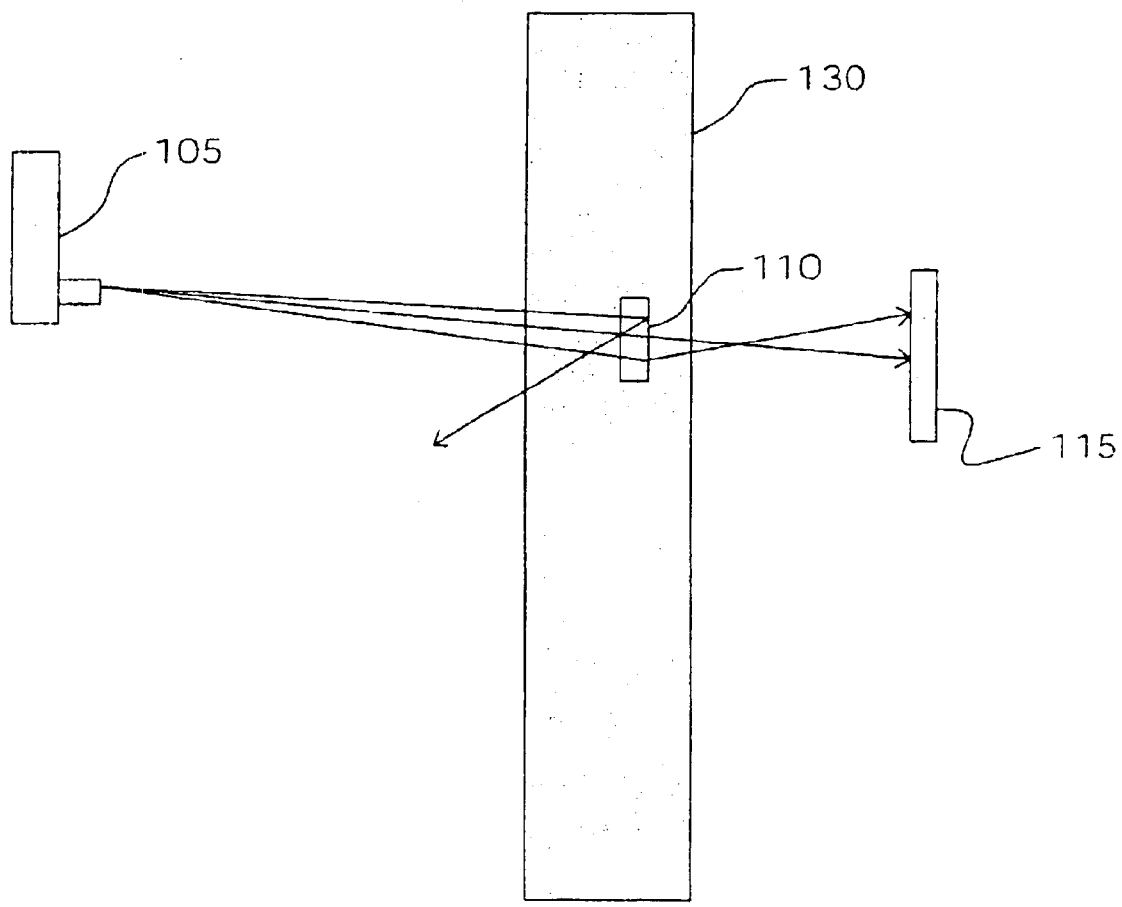
FIG. 1 is a schematic illustrating the configuration used for conventional transmission radiography.
Figure 2:
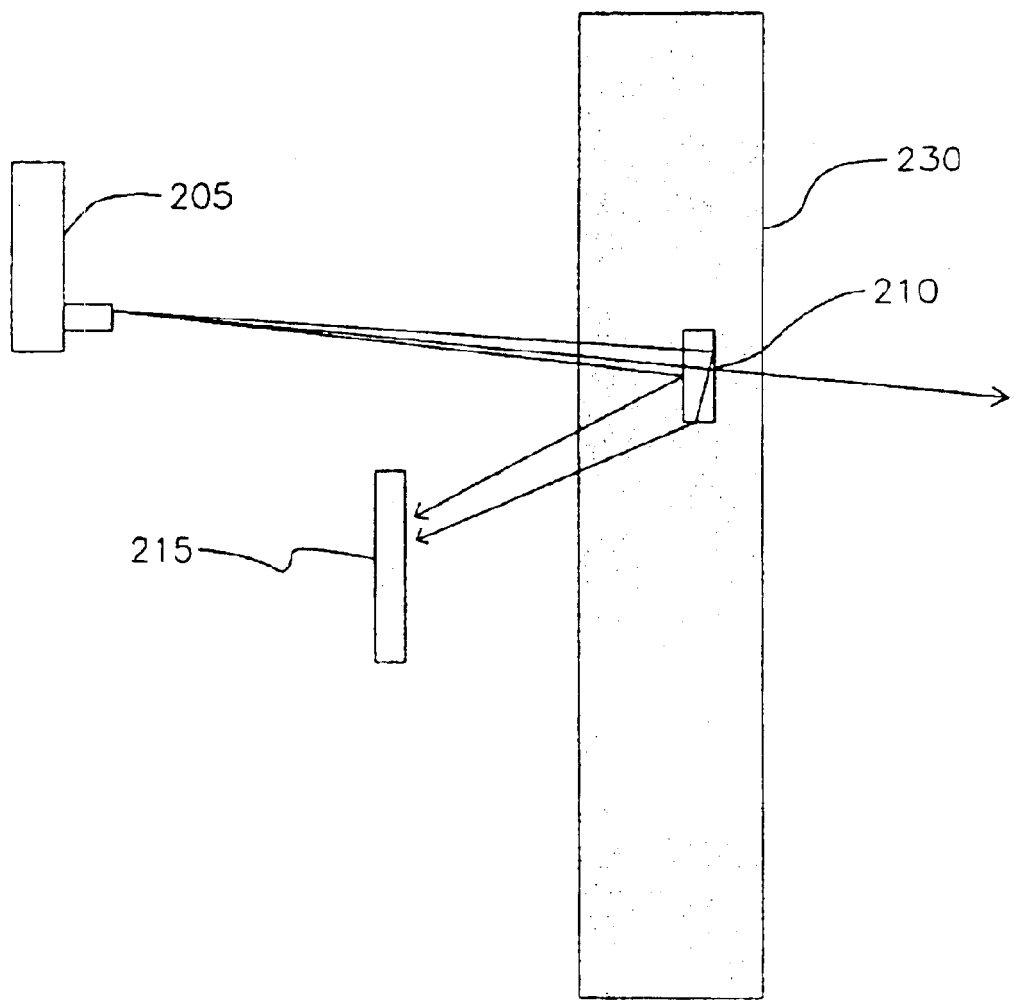
FIG. 2 is a schematic illustrating the configuration used for conventional backscatter radiography.
Figure 3:
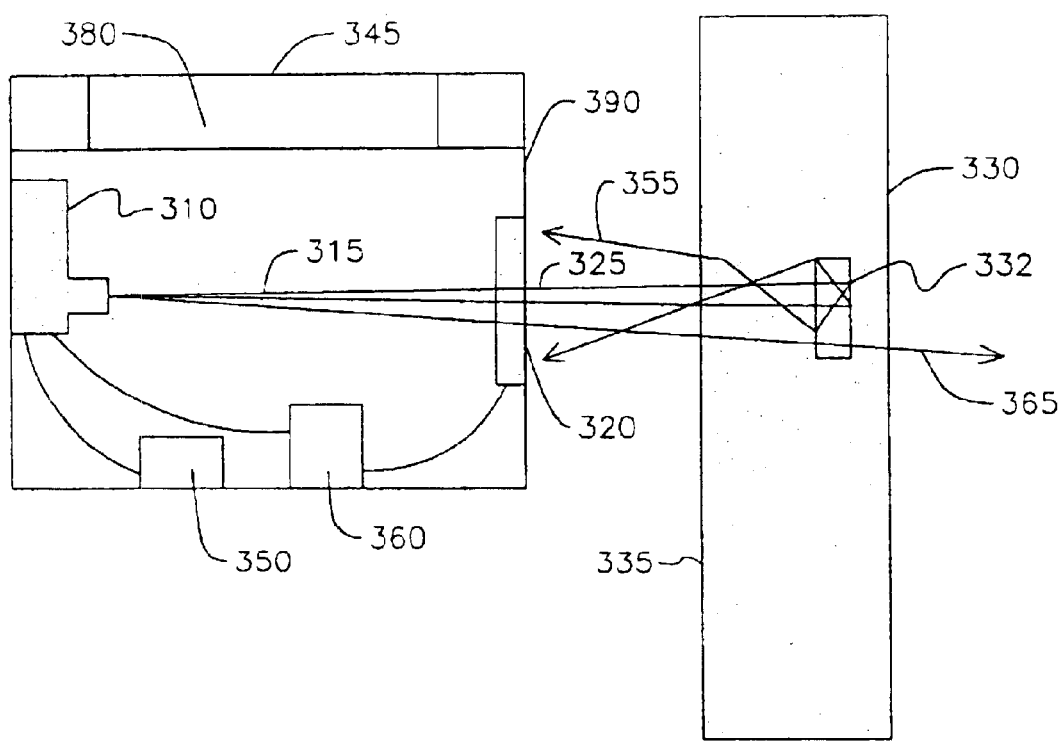
FIG. 3 is a schematic illustrating the configuration used for snapshot backscatter radiography, according to an embodiment of the invention.

FIG. 3 is a schematic illustrating a system configuration which can be used for snapshot backscatter radiography (SBR), according to an embodiment of the invention. A snapshot backscatter radiography (SBR) system 300 includes at least one penetrating radiation source 310 and at least one radiation detector 320, such as a flexible detector sheet. The SBR system 300 can be configured using commercially available radiation generators and detectors. Similar to backscatter radiography, both the radiation source 310 and the radiation detector 320 are disposed on the same side of the object 330 which includes internal detail 332. The surface of the object or the surface of the medium covering the object, such as the earth, is indicated as reference 335.

System 300 can include a radiation source controller 350 and computer 360. Computer 360 preferably includes memory and provides various system functions, such as producing data representing an image of the object interrogated based on radiation data detected by detector 320. A display screen 380 for representing an image of the object interrogated is also preferably provided.

The radiation detector 320 is preferably a digitizing radiation detector-film screen. In this embodiment, computer 350 has at least modest speed and data storage capacity for data processing and driving display 380.

Using the invention, two-dimensional (2D) or three-dimensional (3D) data sufficient to generate an image of the internal structure of objects capable of scattering a portion of incident radiation is acquired in a snapshot illumination of an interrogated area of the object surface. Image data for 2D back-projections can be acquired in a single radiation generator/source burst.

Image data for a 3D display can be acquired if a temporal sequence of data sets is obtained at varying x-ray generator voltages. Higher voltages produce higher energy radiation which penetrates correspondingly deeper into the object. The idea of photon spectrum tomography (Towe & Jacobs, *X-ray Backscatter Imaging*, IEEE Trans., on Biomed.-Engr., BME-28, p. 646–650, 1981) can be exploited to create a 3D image of the interrogated object internal structure. A pulsed radiation (e.g. x-ray) generator with a significant photon energy spectrum variation over the pulse duration provides a useful method of obtaining such information in a single photon source pulse. In this embodiment, the temporal resolution of the detector would need to be sufficient to acquire this 3D image data in a single pulse. Otherwise, temporal gating could be employed for a sequence of generator pulses.

System 300 is generally contained in a protective and supportive housing 345, which is preferably made from aluminum, or other suitable lightweight materials. Housing 345 holds the various components of system 300 in place. Lightweight housing materials facilitate portability of system 300, which can be advantageous in certain applications. The front of housing 390 as well as detector 320 (e.g. a thin sheet) are both preferably made from flexible materials to conform to a variety of desired shapes.

The spacing of detector 320 from source 310 generally depends on the area to be illuminated. For most wide area applications, the spacing from source 310 to detector 320 is generally about the same order of magnitude as the length of detector 320.

The arrangement shown in FIG. 3 implies that the radiation/object interactions of primary consequence are scatterings, although absorption can also be significant. Radiation from the radiation source 310, shown by reference 315, is directed at detector 320 which detects forward radiation 315. The detected radiation pattern is referred to herein as the first-pass data. The detected first-pass data includes information on the spatial variations of the illumination radiation field and the spatial variation of structure and sensitivity of the detector 320.

Detector 320 transmits a portion of the forward radiation received, shown as reference 325, which penetrates surface 335 and strikes internal detail 332 of object 330. The detector medium is generally a detector sheet which provides an area which is at least equal to the illumination area provided by radiation source 310.

The internal detail 332 of object 330 then backscatters a portion of the transmitted radiation 325, shown as reference 355. Preferably, object 310 scatters (reflects) at least 5 to 30% of the illuminating field provided by radiation source 310. For example, a portion of radiation 325 is transmitted through object 330 and is identified in FIG. 3 as transmitted radiation 365. Radiation detector 320 detects some of the backscattered radiation portion 355, the backscattered radiation pattern referred to herein as the second-pass data. Thus, the second-pass data is generated by the backscattered radiation field 355 which emerges from the object or other surface 335 after being scattered by the internal structure of object 330. Data to obtain the desired image of object can be computed by subtracting the first pass data, or an estimate thereof, from the total detector data measured which comprises the sum of the first and second pass radiation data which includes information on the spatial variations of the radiation field and structure of the detector as well as information on the object structure. Alternatively, the desired image can be obtained by subtracting suitably normalized incident (first-pass) radiation data, or estimate thereof, from the backscatter data collected by the detector.

It is expected that achievable detector medium penetration can be >80%, and object medium reflection >50%, resulting in an object internal intensity of >40% of the first-pass intensity. Under these conditions, about 8% of the photons 315 are used to provide data to create the desired image of object 330. This calculation assumes that the energy of the photons are unchanged throughout the process. However, backscatter radiation energy is somewhat lower than transmitted radiation 325, which is itself less than forward radiation 315. Lower backscatter radiation energy can either enhance or decrease the level of the detected backscattered radiation field signal 355 depending on the object and the detector composition.

The SBR method can utilize the steps of digitization of the radiation data received by detector 320. A digital image of the object 330 can then be obtained and displayed on screen 380 through simple data manipulation, such as by computer 360. Digitization also permits digital image enhancement techniques to be applied to the radiation data.

Radiation source 310 can generally be any penetrating radiation source. Radiation source 310 preferably illuminates the entire area to be interrogated. For example, radiation source 310 can comprise an x-ray source, gamma ray source, neutron source or electron beam source. The radiation source 310 is controlled to provide a photon illumination (energy) spectrum averaged optical depth in object 330 to reach the deepest structure detail desired in the image to be about unity (i.e., one x-ray mean-free-path). In the case of an x-ray source, the generator voltage is chosen to provide the desired photon illumination (energy) spectrum. In addition, the radiation intensity provided by radiation source 310 preferably is sufficiently low so as to not saturate detector 320.

Generally, first pass reference (base) data is obtained without object 330 and is stored, such as in memory provided by computer 360, prior to interrogating object 330. To minimize drift, it is preferred the base data be updated periodically, such as every day or two, or upon a change of configuration, or a change in source energy. Since only a transmitted reference image is desired, the base radiation data is preferably acquired in an environment which does not backscatter significant radiation back to detector 320. For example, a perfect absorbing medium would be ideal. In practice, an empty room may provide a low backscatter environment. The base radiation data can then be subtracted from the overall radiation detected which includes information from both the detector structure and the spatial variation of the radiation source field as well as the object structure to provide data which permits generation of the desired image of object 330.

Figure 4:
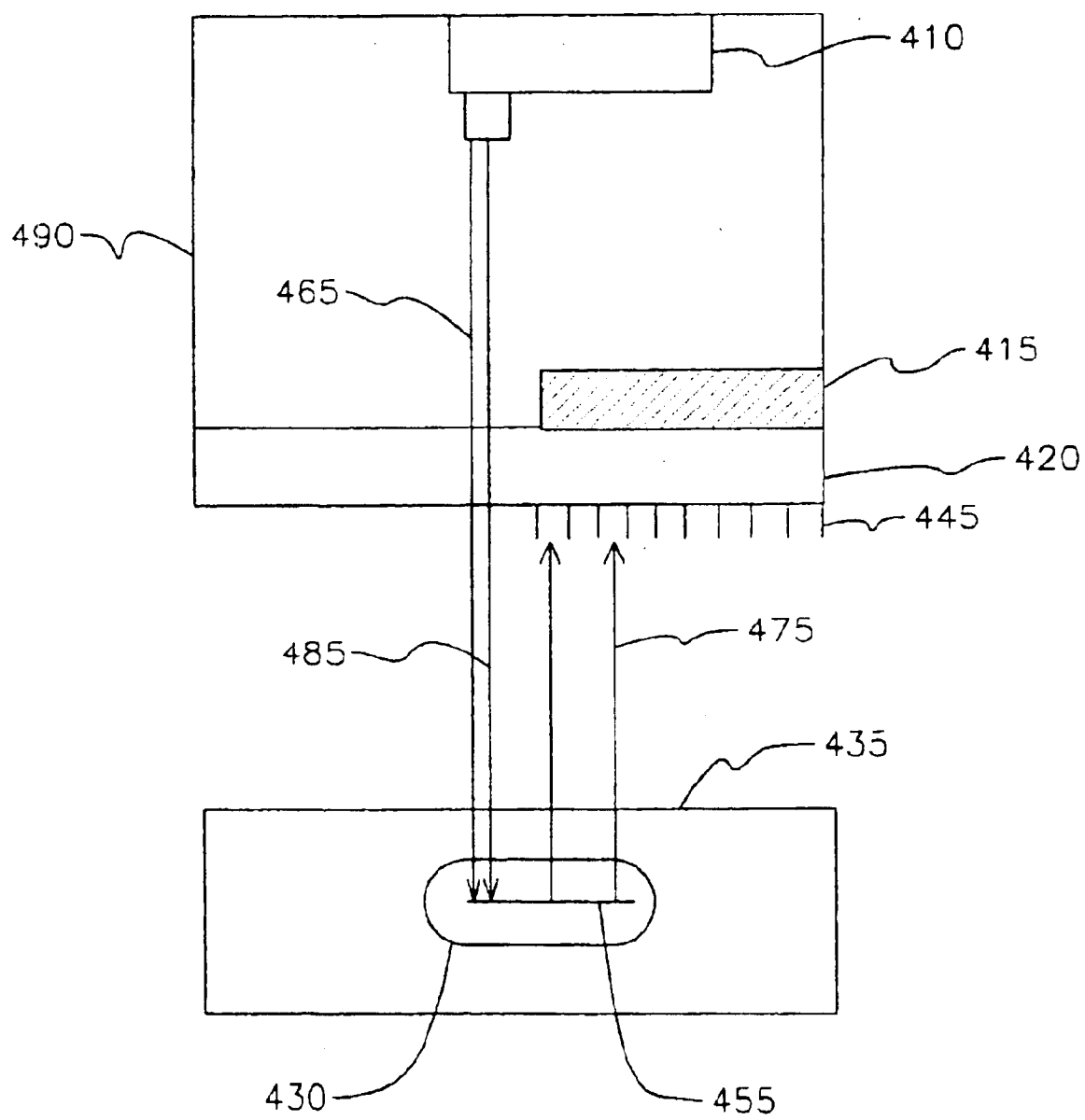
FIG. 4 is schematic illustrating an alternate SBR configuration including collimators which emphasizes the lateral migration signal component of the backscatter radiation signal, according to an embodiment of the invention.

A system 400 including one or more optional collimating sheets 445 is shown in FIG. 4. The plurality of collimator plates 445 are oriented essentially perpendicular to the surface of detector 420 and are disposed between the detector and the object being interrogated beneath absorptive strip 415. The collimating sheets 445 enhance the Compton backscatter imaging. (CBI) process for photons which experience increased migration along directions perpendicular to the illumination direction, such as along the imaged plane in SBR. This data acquisition variant can be helpful for the detection and imaging of small, lateral material structure or defects along planes parallel to the object surface, such as feature 455, including small diameter channels, or thin, delaminated regions which are parallel to an object surface. Conventionally applied collimators can also be used to improve image resolution by limiting beam spot size, but generally also increase measurement time.

System 400 includes an absorptive strip 415 which functions as a shutter which is disposed between the radiation source 410 and the radiation detector 420. Absorptive strip 415 can comprise a lead strip. Absorptive strip 415 blocks transmission of the forward radiation beam 465 over a portion of the area of detector 420. The beam transmitted through detector 420 is identified as reference 485. Housing 490 is also provided.

The object (or volume interrogated) 430 shown includes a crack or other void which provides an airspace 455. Object 430 is shown buried in a medium having a surface 435. The object/medium arrangement is essentially analogous to the arrangement when a land mine is buried in the earth. Land mines are known to include air gaps to permit the fuse mechanism to function properly and to provide directional blasts.

Radiation reflected from object 430 is indicated as backscatter beam 475. Airspace 455 permits significantly enhanced lateral migration of radiation along its length. This lateral enhancement results in a larger percentage of radiation transmitted through detector 420 to fit between laterally positioned adjacent collimator plates and reach detector 420 for detection as compared to when object 430 does not include airspace 455. Thus, when the region being interrogated does not include any measurable airspace 455, the signal detected by detector 420 beneath reflective strip 415 will be significantly less as compared to when object 430 include airspace 455. Thus, system 400 can be used to identify structures such as landmines, delaminations and other structures which provide significant air spaces.

SBR is well suited to planar object interrogation of surfaces for both placement of the detector and interpretation of the scattered radiation produced image. Independent of the flexibility of the detector medium, it is estimated that SBR can provide useful images of internal structure details of objects if the image size dimension is less than about one-third the radius-of-curvature of the interrogated region object surface. If the detector (e.g. film) is sufficiently flexible to conform to the object surface, this limit should increase to about one-half, or more, depending on the distance to the radiation (e.g. x-ray) generator focal spot from the object surface.

Radiography applications, wherein internal structure near the surface of an object is to be imaged, can benefit significantly from the backscatter point of view provided by SBR. However, unlike backscatter radiography, the radiation detector 320 is disposed in the radiation path so that the radiation which reaches the object 330 first passes through the radiation detector 320. Disposing the detector 320 in the radiation path as shown in FIGS. 3 and 4 provides certain advantages. In particular, the ability to provide a snapshot image of object 330 without the need for mechanical scanning of the radiation source or object rotation.

The temporal history of radiation in SBR is unlike either conventional transmission radiography or conventional backscatter radiography. Source generation of penetrating radiation results in a first-pass through detector 320. This step is not provided in either conventional transmission radiography or backscatter radiography. Interaction with internal structure of object 330 produces reflective scattering which results in a second-pass through radiation detector 320. This step is similar to conventional backscatter radiography, although the radiation incident on the object is transmitted through the radiation detector in SBR, whereas the radiation incident on the object is provided directly from the radiation source in conventional backscatter radiography.

A variety of image detection technologies can be used with the invention. The detector 320 generally needs to store base image data. The detector needs to permit significant radiation to be transmitted therethrough. The detector 320 also needs to be capable of receiving multiple images, i.e., be reusable with a minimum of drift.

For example, in the case of x-ray radiography where a large area image is desired, there are at least two available x-ray detector technologies which can be used with the invention. The photostimuable phosphor-based imaging plate (commonly referred to as computed radiography, or CR), as well as an amorphous silicon panel (ASP) conversion screen bonded to an array of photosensitive diodes.

The CR imaging medium is generally thin, uniform, and flexible. X-ray sensitivity and image spatial resolution are sufficient for most applications. Significant care must be exercised in the time between latent image acquisition and photo stimulation in the image reading process including light exclusion. As the technique is conventionally applied, there is a separate image reader device and the imaging plate (film) is transferred from the x-ray illumination device to the reader for image digitizing and display. For application of the CR method to an SBR system, it would be advantageous if image exposure, reading, digitization, and display were accomplished in the same device eliminating the physical transfer of the imaging plate in the process.

The geometric featureless quality and physical flexibility of the CR image plate imply a uniform first-pass image and easily-obtained conformity of image acquisition geometry to the object surface. These properties imply relatively straight-forward analysis of the acquired image and post-acquisition processing (e.g., subtraction of the first-pass image).

Most ASP detectors are neither thin nor homogeneous, but there are panel models where the associated amplifiers and voltage supplies are placed to the side of the imaging area. Typical panels are heavily shielded against x-ray penetration from the rear which negates the geometric necessities of the SBR system.

A major advantage of an ASP detector-film is the inherent, single-step image acquisition process. Data from a sequence of images can be acquired and stored for processing. Image differences obtained from a series of varying x-ray generator voltages can be employed to yield 3D images of internal structure. Image differences obtained from a series of x-ray generator pulses can also form the basis of analysis of the dynamic response of internal structure, such as suggested in the development of dynamic radiography (Kenney & Jacobs, *Research Techniques in Nondestructive Testing*, Chapter 6, p.217–243, Edited by Sharpe, Academic Press, 1977). With sufficient temporal resolution of the panel, a single x-ray generator pulse with time-varying spectrum can be employed to efficiently acquire data for either of these applications.

CCD or other chip-based detectors may also be use with the invention in applications where a large area image is not required. Chip based detectors are generally useful when the area to be interrogated is relatively small, such as on the order of several ems, tens of $\mu$ms, or hundreds of $\mu$ms, such as a region on an integrated circuit.

The equivalent of an optical snapshot camera is often desirable for many applications, but has previously only been available using conventional transmission radiography. Unlike conventional transmission radiography which uses transmitted radiation, the SBR system and method described herein advantageously enables snapshot radiography utilizing reflected radiation, for example for applications where a detector cannot be placed behind the object to be interrogated. The compact size, simple system configuration, and small time increment for image data acquisition, all contribute to efficiency accuracy and viability of many diagnostic and/or process control applications for SBR.

A clear benefit of the SBR approach is for radiography applications in which there is only one-sided access to the object. For example, scanning electron microscopes (SEM) are commonly used in integrated circuit failure analysis and some process control which requires resolution beyond that provided by standard optical inspections. One reason for common use of SEMs in integrated circuit processing is because of high image resolution compared to standard optical inspection tools. Moreover, transmission radiography is generally not possible for interrogating integrated circuits due to the presence of one or more heavily absorptive surfaces. For example, gold may coat the backside of the chip. Significantly, unlike SBR systems which can interrogate below the surface of a sample, conventional SEMs cannot interrogate regions below the surface. In addition, SBR systems are expected to be inexpensive relative to SEMs. As noted above, the SBR system can provide improved image resolution, and provide a resolution comparable to that obtainable from conventional SEMs by including one or more collimators system to reduce the beam size as required for the desired resolution level.

The invention is also helpful where an internal structure element is difficult, or impossible, to image by conventional transmission radiography or even conventional backscatter radiography because of amplification of image contrast during the subsurface migration, such as lateral migration, of the interrogating radiation produced by SBR which can be selectively sensed by proper design of the radiation detector components.

The invention is expected to have a variety of applications as it enables rapid snapshot images of an object or volume of interest and can also be a portable system. For example, the invention can be used as a land mine detection system, for either military or humanitarian use to identify buried land mines. Most buried land mines are made of predominantly plastic which makes it almost impossible to detect the mines accurately with conventional detection techniques. Using the SBR system and method, explosives and plastics reflect more photons than soil does, and scatter the photons more widely, which can create more accurate images of the mines. Rocks, wood, roots and other materials create very different images and are generally not confused with land mines using SBR.

The system can be small and lightweight, making it readily mobile. Thus, soldiers can carry an SBR system and interrogate the path in front of them before proceeding. Alternatively, landmine detectors can mounted on a vehicle to create mobile land mine detectors.

In addition, the invention is expected to be useful for rapidly screening articles within containers, such as luggage or cargo entering airports. As compared to current x-ray based conventional transmission or backscatter scanning detectors, the invention is expected to be manufacturable at a significantly reduced cost since it does not require mechanical scanning of the object or any system component. In addition, the SBR system can be portable, and provide images faster than conventional scanning systems. As noted above, the SBR system can also detect explosives, such as plastic explosive, that are generally undetectable by conventional systems used at airports.

EXAMPLE

The present invention is further illustrated by the following example. The example is provided for illustration only and is not to be construed as limiting the scope or content of the invention in any way.

SBR was tested in a single measurement which successfully imaged a high-contrast feature in an optimal configuration of an SBR system using x-rays and a computed radiography (CR) screen detector with the associated image reader replacing the image-analyzing computer. The object (and "structure") was a plastic block on the interrogated surface which included a small (1 cm×1 mm×0.1 mm thick) strip of lead. From the SBR image obtained the lead strip was clearly visible, with about 0.1 mm resolution provided.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A snapshot backscatter radiography (SBR) system, comprising:
    at least one penetrating radiation source, and
    at least one radiation detector, wherein said radiation detector is interposed between an object to be interrogated and said radiation source, said radiation detector transmitting a portion of incident radiation from said radiation source to said object, wherein a portion of radiation scattered by said object is detected by said detector.

2. The system of claim 1, wherein said penetrating radiation source comprises at least one selected from the group consisting of an x-ray, gamma ray, neutron and electron beam source.

3. The system of claim 1, wherein said detector comprises a digitizing field screen.

4. The system of claim 1, further comprising a computer for receiving radiation data from said detector and for performing data and image processing.

5. The system of claim 1, wherein said system provides 3 dimensional (3-D) radiation image data.

6. The system of claim 5, further comprising a radiation source controller.

7. The system of claim 6, wherein said radiation source controller directs said radiation source to provide at least one of multiple bursts at varying radiation energy or temporal variation of a radiation energy spectrum provided by said radiation source.

8. The system of claim 1, wherein said detector comprises a photostimuable phosphorous-based image plate.

9. The system of claim 1, wherein said detector comprises an amorphous silicon panel.

10. The system of claim 1, wherein at least one collimating sheet is disposed between said object and said detector.

11. The system of claim 1, wherein said object comprises an integrated circuit.

12. A snapshot backscatter radiography (SBR) based land mine detection system, comprising:
    at least one penetrating radiation source, and
    at least one radiation detector, wherein said radiation detector is interposed between a volume of earth to be interrogated and said radiation source, said radiation detector transmitting a portion of incident radiation from said radiation source to an object buried in said volume of earth, wherein a portion of radiation scattered by said object is detected by said detector.

13. The system of claim 12, wherein said radiation source comprises an x-ray source.

14. The system of claim 12, wherein said system further comprises a vehicle.

15. A snapshot backscatter radiography (SBR) based luggage or cargo screening system, comprising:
    at least one penetrating radiation source, and
    at least one radiation detector, wherein said radiation detector is interposed between luggage or cargo to be interrogated and said radiation source, said radiation detector transmitting a portion of incident radiation from said radiation source to said luggage or cargo, wherein a portion of radiation scattered by said luggage or cargo is detected by said detector.

16. A snapshot backscatter radiography (SBR) based integrated circuit inspection tool, comprising:
    at least one penetrating radiation source, and
    at least one radiation detector, wherein said radiation detector is interposed between an integrated circuit to be interrogated and said radiation source, said radiation detector transmitting a portion of incident radiation from said radiation source to said integrated circuit, wherein a portion of radiation scattered by said integrated circuit is detected by said detector.

17. The system of claim 16, wherein said detector comprises a CCD detector.

18. The system of claim 16, wherein said penetrating radiation source provides selectable radiation energy, wherein a 3-D image of said integrated circuit can be obtained without physical scanning by compiling radiation data at a plurality of radiation energies.

19. A snapshot backscatter radiography (SBR) method for imaging an object, comprising the steps of:
    directing penetrating forward radiation through a detector to an object to be interrogated, said detector transmitting a portion of said penetrating radiation to said object, wherein said object backscatters radiation toward said detector, and
    generating an image of said object.

20. The method of claim 19, wherein said forward radiation comprises multiple bursts at varying radiation energy, said method further comprising the step of forming a 3-D image of said object.

21. The method of claim 19, wherein at least one collimating sheet is disposed between said object and said detector, further comprising the step of collimating at least one of said forward radiation and said backscattered radiation.

22. The method of claim 19, further comprising the step of applying a deconvolving image enhancement technique to reduce image blurring.

23. The method of claim 19, wherein said image is formed by subtracting said forward radiation detected at said detector or an estimate of said forward radiation detected at said detector from all radiation detected by said detector.

24. The method of claim 19, wherein said image is formed by subtracting normalized forward radiation data detected at said detector or an estimate thereof, from backscatter radiation detected by said detector.

* * * * *